(12) United States Patent
Huang (10) Patent No.: US 6,871,545 B2
(45) Date of Patent: Mar. 29, 2005

(54) SYSTEM AND METHOD FOR MEASURING STIFFNESS IN STANDING TREES

(75) Inventor: Chin-Linn Huang, Bellevue, WA (US)

(73) Assignee: Weyerhaeuser Company, Federal Way, WA (US)

( * ) Notice: Subject to any disclaimer, the term of this patent is extended or adjusted under 35 U.S.C. 154(b) by 20 days.

(21) Appl. No.: 10/600,933

(22) Filed: Jun. 20, 2003

(65) Prior Publication Data

US 2005/0005699 A1 Jan. 13, 2005

(51) Int. Cl.[7] .......................... G01N 29/24; G01N 29/18
(52) U.S. Cl. ............................................. 73/597; 73/644
(58) Field of Search ........................ 73/597, 598, 632, 73/644, 579

(56) References Cited

U.S. PATENT DOCUMENTS 3,066,525 A * 12/1962 Harris .......................... 73/644
6,467,352 B2 * 10/2002 Schafer et al. ................ 73/597

* cited by examiner

Primary Examiner—John E. Chapman
(74) Attorney, Agent, or Firm—Christensen O'Connor Johnson Kindness, PLLC (57) ABSTRACT

A system for non-destructive testing using acoustic techniques includes first and second measuring probes and an electronic unit. Each probe includes a penetrating end and a retaining flange end. Each probe further includes a handle slideably coupled to the probe and a transducer for detecting stress waves. The probes are lightweight, portable, and rugged for field testing wood products.

20 Claims, 4 Drawing Sheets

SYSTEM AND METHOD FOR MEASURING STIFFNESS IN STANDING TREES

FIELD OF THE INVENTION

The present invention is directed to systems and methods for non-destructive testing, and in particular, to non-destructive testing of wood products, including standing trees, felled trees, logs, dimensional lumber, and the like.

BACKGROUND OF THE INVENTION

A major source of raw material for the wood processing industry is supplied by trees grown on intensively managed plantations or "tree farms". Over the years, nurseries producing seed for plantation trees have used intensive genetic selection to improve such heritable traits as rapid growth, straightness of stem, reduced limb diameter, and other desirable characteristics, and silvicultural innovations, such as better regeneration, fertilization, vegetation control, thinning, and pruning, have significantly increased the growth rate and visual quality and greatly shortened the rotation age of plantations. Consequently, depending on the species and growth locale, plantation trees for saw logs are usually harvested on a 20–50 year growth cycle, with various pine species being typically harvested 20–30 years after planting.

The raw material supplied to mills from plantations has characteristics that have been shown to be more variable due to the plantation's shortened growth cycle, as will now be explained. Most conifer species produce wood having so-called juvenile characteristics during the first 10–20 years of their growth. This juvenile wood is characterized by thinner cell (tracheid) walls, a higher microfibril angle in the tracheid walls, lower specific gravity, increased lignin, increased hemicellulose, and less cellulose than those of mature trees. High microfibril angle, low density, and varying quantities of chemicals in juvenile wood are the fundamental properties that impair the quality (i.e., strength and dimensional stability) of the wood products. After about 12–20 years of growth, density begins to increase as wood is laid down at greater distances from the pith and the microfibril angle begins to decrease until the wood has acquired "adult" properties. Under normal conditions during the wood's "mature stage", density, microfibril angle, and chemicals of the wood remain essentially constant during the remaining years of the tree's growth. Therefore, logs harvested from the short-rotation plantations may be prone to both warp and lower stiffness.

Dimension lumber is the major construction material for residential and commercial buildings in North America. Stiffness and straightness are the critical attributes of structural lumber and engineered wood products for builders, the main customers of lumber. Failure to make the products that will meet the specifications of the builders potentially costs the commercial forestry industry large sums of money. For instance, the influx of plantation wood has made it more difficult for mills to produce stiff and straight lumber at prices the builders are prepared to pay, which is currently causing wood from plantations to be downgraded, resulting in lost market share to substitutes such as steel, vinyl, and engineered wood products as a construction material. As such, the earlier the industry can select and sort the wood quality during the commercial forest cycle, from breeding to products, the more efficient the industry will be. Therefore, there is a need in the industry to have testing techniques that predict wood properties, particularly stiffness, of standing trees, preferably in the early phases of a plantation forest cycle.

To address such an ongoing need of the commercial forest industry, non-destructive testing devices and methods have been developed that utilize acoustic techniques for non-destructive testing of wood properties, such as warp propensity, stiffness, and degree of decay, of standing trees or felled logs. Several of these devices and methods are disclosed in U.S. Pat. No. 6,347,551 B1, U.S. Pat. No. 6,276,209 B1, U.S. Pat. No. 6,026,689, U.S. Pat. No. 6,305,224 B1, and U.S. Patent Application Publication US 2003/0079544 A1 and PCT Publication No. WO 02/29398 A1, all of which are hereby incorporated by reference.

While these prior art devices and methods are adequate in testing wood properties in either standing trees or felled logs, the devices and methods are not without their deficiencies or disadvantages. For instance, the prior art devices and methods were not designed for rapid field testing of stiffness properties in standing trees or felled logs. Specifically, some of the devices are quite large and must be used at the mill, while others require an exorbitant amount of time to complete the testing of one tree or log and are designed for experimental testing, thus, may be damaged easily and are frequently inoperable if repeatedly used in field testing.

SUMMARY OF THE INVENTION

The present invention addresses the deficiencies in the prior art and others by providing an in-situ non-destructive evaluation system that is field-portable, lightweight, and field-rugged/reliable for wood quality surveying. The system includes two integrally constructed measuring probes connected in electrical communication to an electronic unit. Each of the measuring probes may be inserted into and extracted from the wood product with one hand, thus improving the speed in which a plantation or "tree farm" may be tested. In fact, experimental trials have shown that a field operator utilizing a system constructed in accordance with the present invention may test young plantations, on average, 100 trees per hour. The benefits of which may allow for plantations to be tested more frequently than is currently available using prior art devices, and a reduction in total man hours, and thus, the cost needed to complete the testing. The present invention also includes unique measuring probes and a method for non-destructively testing the wood product.

In accordance with aspects of the present invention, a system for non-destructive testing of wood products is provided. The system includes a first integrally formed handheld measuring probe having a body that includes a shaft defining a first impact surface, a spike fixedly coupled to one end of the shaft, a transducer in contact with the spike for detecting a stress wave imparted thereto and outputting a signal indicating the presence of a stress wave, and a handle slideably coupled to the shaft. The system also includes a second integrally formed handheld measuring probe having a body that includes a shaft, a spike fixedly coupled to the shaft, a transducer in contact with the spike for detecting a stress wave and outputting a signal indicating the presence of a stress wave, and a handle slideably coupled to the shaft. The system further includes an electronic unit including a timing device. The electronic unit is coupled in electrical communication with the transducer of the first measuring probe and the transducer of the second measuring probe for receiving the outputted signals therefrom. The electronic unit determines the travel time of the stress wave from the transducer of the first probe to the transducer of the second probe.

In accordance with another aspect of the present invention, a portable measuring probe is provided. The probe includes an elongated body including a shaft, a spike fixedly coupled to one end of the shaft, a transducer in contact with the spike for detecting a stress wave imparted thereto and outputting a signal indicating the presence of a stress wave, and a handle slideably coupled to the shaft.

In accordance with yet another aspect of the present invention, a method for testing the stiffness in wood products using a non-destructive testing system is provided. The system includes a first measuring probe, a second measuring probe, and an electronic unit. Each probe has a spike, a shaft, first and second contact surfaces at the proximal and distal ends of the shaft, a handle slideable coupled to the shaft between the first and second contact surfaces, and a transducer connected in electrical communication with the electronic unit. The method comprises inserting the spike of the first measuring probe into the wood product and driving the spike further into the wood product by sliding the handle in the direction of the spike and impacting the first contact surface. The spike of the second probe is then inserted into the wood product a spaced distance from the first probe and is driven further into the wood product by sliding the second probe handle in the direction of the second probe spike and impacting the first contact surface of the second probe. Next, a stress wave is generated at the first probe, and the time taken by the stress wave to travel from the first probe to the second probe is determined.

It will be appreciated that testing a forest of standing trees utilizing a system in accordance with the present invention may allow the relative quality of standing trees, and thus, the value of the forest, to be more accurately assessed. This may allow trees of lessor quality to be identified and thinned, thus increasing the average value of the forest. Alternatively, the lesser value trees can be felled and taken for use in less valuable or non-structural wood products, such as chips or furniture, thereby providing improved access to the high quality trees, and thereby, potentially reducing the damage in removing such high quality trees. Furthermore, trees of lesser quality can be identified prior to shipment to the mills, thus improving the efficiency, and potentially the profitability to both mills and forest owners alike.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

The present invention will now be described with reference to the accompanying drawings where like numerals correspond to like elements. The present invention is directed to a system for non-destructive evaluation or testing of wood products, including standing trees, felled trees, logs, dimensional lumber, and the like, using acoustic testing methods. Additionally, the present invention is directed to an improved integrally formed first measuring probe and an improved integrally formed second measuring probe suitable for use by the system and others for non-destructive evaluation and testing. The present invention is further directed to a method for non-destructive testing of standing trees. While one embodiment of the non-destructive evaluation system will be described with reference to its evaluation or testing of wood products, and in particular, standing trees, the system may be used in other applications desiring the benefits of non-destructive evaluation. Thus, the following description is meant to be illustrative and not limiting the broadest scope of the invention, as claimed.

Figure 1:
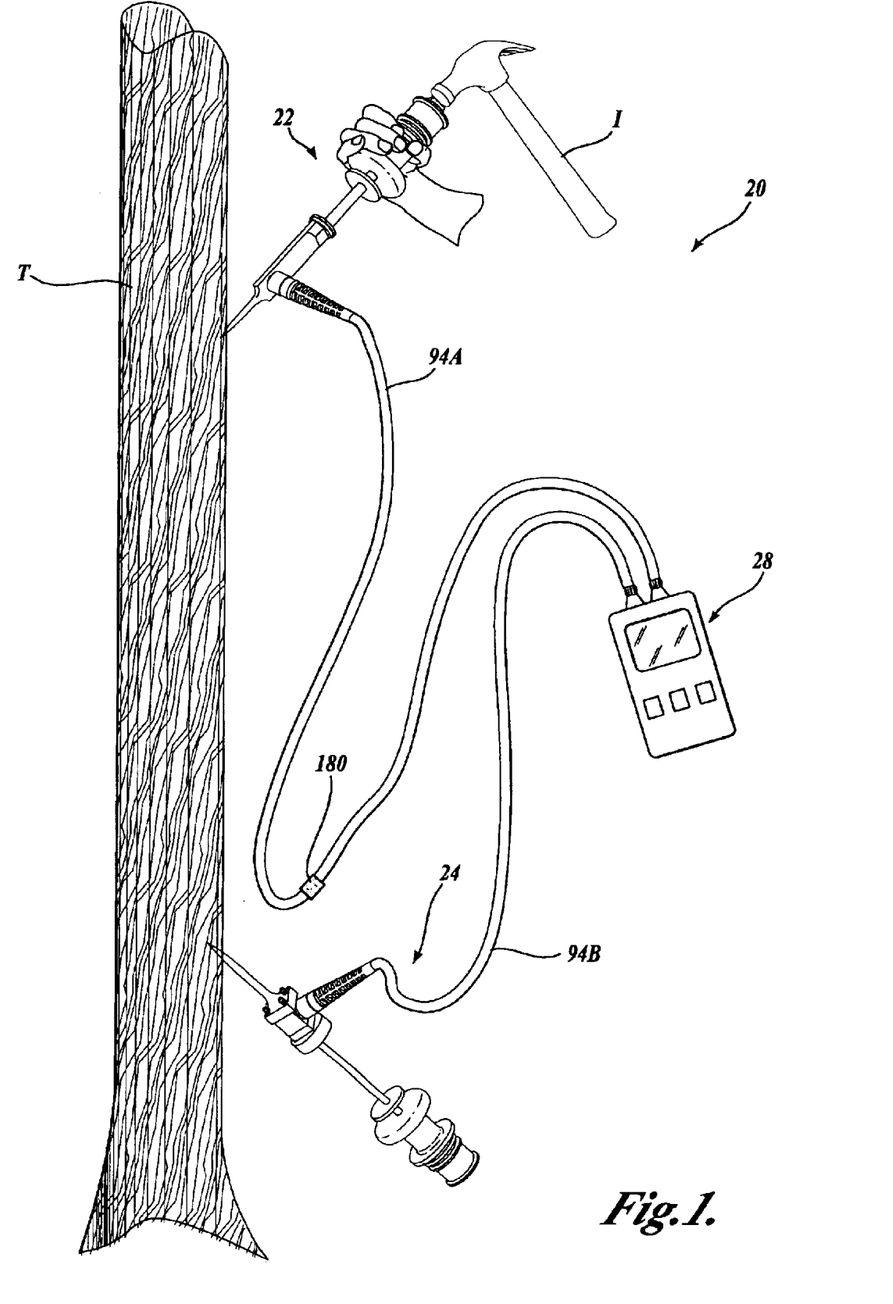
FIG. 1 is a perspective view of a system for non-destructive testing of wood products in accordance with the present invention.

One illustrative embodiment of a non-destructive evaluation system, generally designated 20, formed in accordance with the present invention is shown in FIG. 1. The system 20 comprises a first or start measuring probe 22 and a second or stop measuring probe connected in electrical communication with an electronic unit 28. In operation, the start measuring probe 22 and the stop measuring probe are attached to a tree T a spaced distance from one another. A sound or stress wave is induced into the tree T at the start measuring probe 22, and the time required by the stress wave to travel from the start measuring probe 22 to the stop measuring probe 24 is determined by the electronic unit 28. The resulting time determined by the electronic unit 28 may be converted into a velocity from the known equation (v=d/t), if desired, by knowing the spaced distance between the start and stop measuring probes 22 and 24. Either the time measurements or velocity calculation may, in turn, be used to determine the stiffness of the tree, and thus, the quality of the tree.

Figure 2:
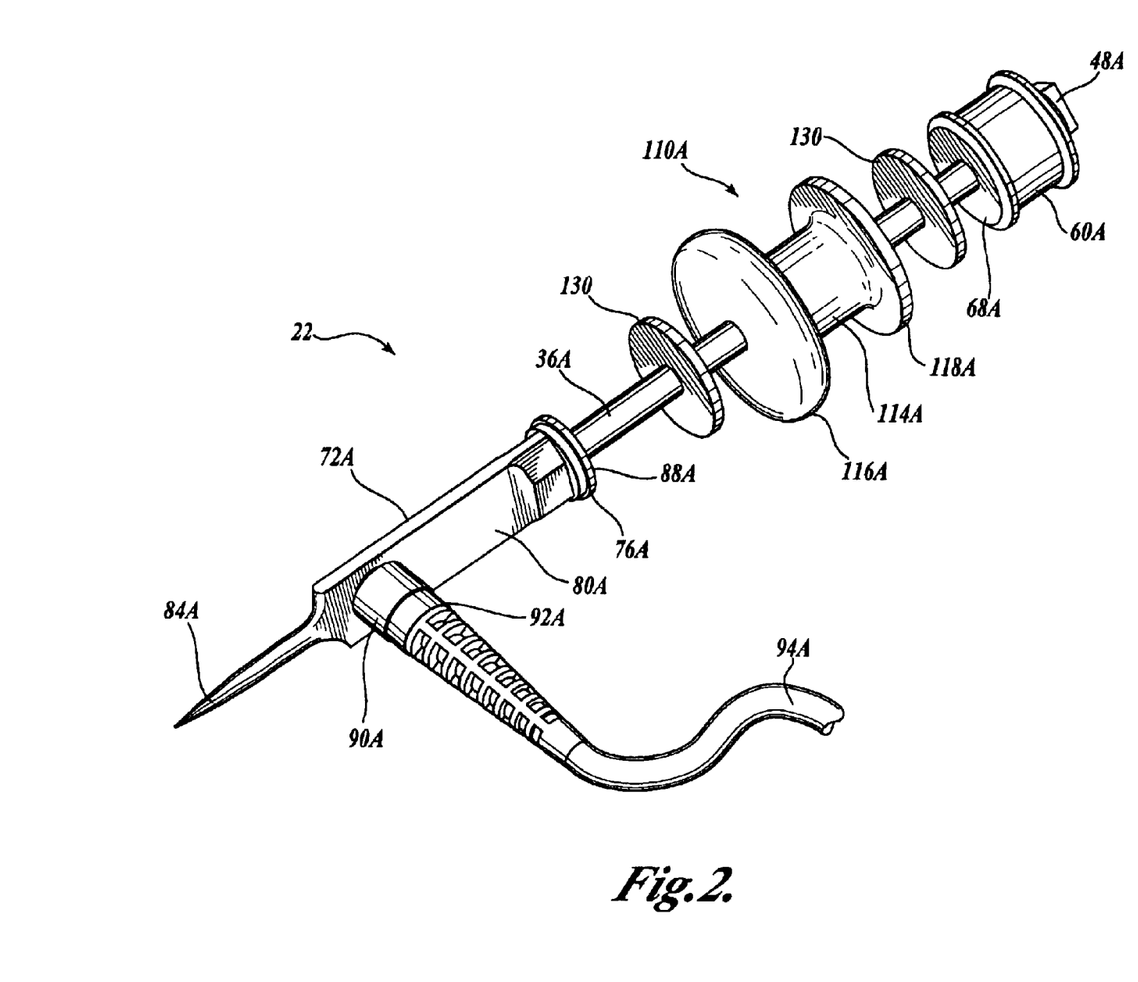
FIG. 2 is a perspective view of an integral measuring probe of the system shown in FIG. 1.
Figures 5, 6:
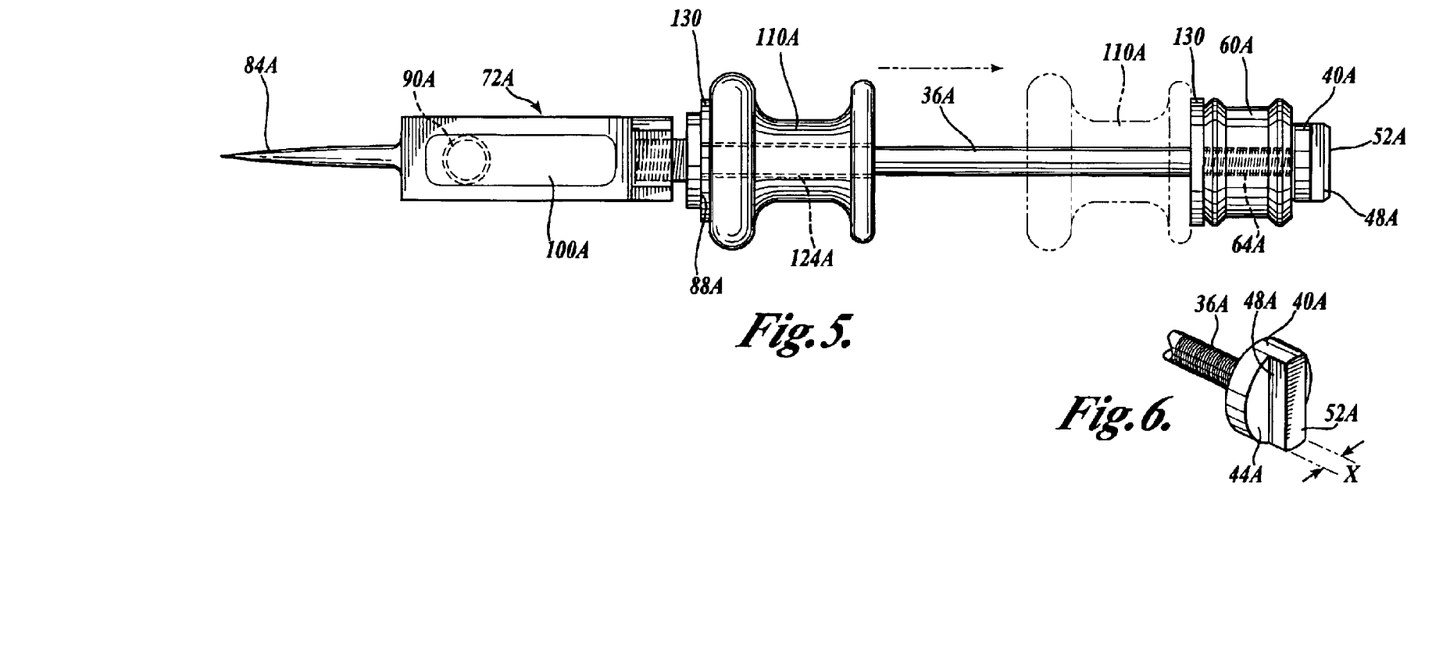
FIG. 5 is a side elevational view of the integral measuring probe of FIG. 2.
FIG. 6 is a partial perspective view of the end of the shaft of the measuring probe of FIG. 2.

Referring now to FIG. 2, there is shown a perspective view of the start measuring probe 22. The start measuring probe 22 is integrally constructed of a size and weight suitable to be repeatedly carried and operated by one hand of a field operator for rapidly testing a plurality of wood products. The measuring probe 22 comprises an elongate shaft 36A, preferably metallic, that terminates at one end as a cylindrical retaining flange 40A (see FIG. 5). The diameter of the retaining flange 40A may be approximately three times the diameter of the shaft 36A. As best shown in FIG. 6, the retaining flange 40A defines an end face 44A from which a projection 48A extends across the retaining flange through the center thereof. The projection 48A defines a planar impact surface 52A substantially orthogonal to the longitudinal axis of the shaft 36A. As will be described in detail below, a hammer, mallet or other impact tool I (see FIG. 1) will be used to strike the impact surface 52A, which in turn, generates a stress wave that transmits through the shaft 36A. While the geometry of the projection is shown as rectangular, other geometries may be practiced with the present invention, such as cylindrical, conical, frusto-conical, pyramidal, frusto-pyramidal, to name a few. It will be appreciated that these of other geometries define a contact surface or point in which to strike with the impact tool.

In accordance with an aspect of the present invention, the width wise dimension of the impact surface 52A, shown as "x", is preferably configured to be approximately ½ the size or smaller than the width wise dimension of the striking surface of the impact tool so that the detected signal is more stable. The configuration of the projection 48A and impact surface 52A is thought to act as a wave guide, and thus, the injected stress wave is more aligned and focused. In one embodiment of the present invention, the projection is ¼ inch tall, ¼ inch wide, and 1 inch thick.

Referring now to FIGS. 2 and 5, an optional stop collar 60A is fixedly attached to the end of the shaft 36A, adjacent the retaining flange 40A. The stop collar 60A is cylindrical in shape and includes a bore 64A through which the shaft 36A is routed when assembled. The stop collar 60A is preferably constructed from a strong yet lightweight material, such as plastic or the like. At the end of the stop collar 60A, opposite the retaining flange 40A, there is defined a planar contact surface 68A. The planar contact surface 68A is generally orthogonal to the longitudinal axis of the shaft 36A. In one embodiment, the stop collar 60A may be fixedly connected to the end of the shaft 36A by matable surfaces of optional external threads on the end of the shaft adjacent the retaining flange 40A and the optional cooperating threads formed in the bore 64A, as best shown in FIG. 5.

Referring to FIG. 2, the elongate shaft 36A is coupled at its other end to a spike 72A, preferably metallic, having a cylindrical base flange 76A, a somewhat flat middle portion 80A, and a penetrating free end 84A. In the embodiment shown in FIG. 5, the shaft is coupled to the spike 72A through cooperating matable treads; however, the shaft may alternatively be coupled to the spike by other methods, such as welding. The base flange 76A defines a planar contact surface 88A that faces the stop collar 60A and is orthogonal to the longitudinal axis of the shaft 36A. The middle portion 80A includes a connector fitting 90A attached to or integrally formed on one side thereof. The connector fitting 90A is configured for connection to a cooperating connector 92A attached to the end of a flexible sleeve 94A that extends from the measuring probe 22 to the electronic unit. Wires or other signal transmitting devices (not shown) are routed through the flexible sleeve 94A and connected in electrical communication with a transducer 100A (see FIG. 5). The transducer 100A contacts the middle portion 80 on the opposite side of connector fitting 90A and is affixed thereto via chemical fastening methods, such as epoxy. The middle portion 80A may include a channel groove (not shown) for receiving the transducer 100A, and/or the transducer may be covered by a thin layer of rubber or silicone for improved ruggedness and reliability, if desired.

The transducer 100A may be an accelerometer of the piezo-electric type and is shock resistant. The transducer 100A is designed to detect a stress wave generated by an impact tool impacting the impact surface 52A and imparted on a wood product such as tree T, and is capable of outputting a signal (e.g., a voltage) indicating the presence of such a stress wave. The frequency response of the transducer 100A may be chosen for its particular application. For example, during normal forest work, a frequency response of less than 3000 Hz is adequate, but wider ranges may be advantageously used. One suitable transducer 100A that may be practiced with the present invention is item no. PZ02, from Images SI Inc., Staten Island, N.Y.

As best shown in FIGS. 2 and 5, the start measuring probe 22 further includes a handle 110A slideably mounted on the shaft 36A between the stop collar 60A and the base flange 76A. The handle 110A has a generally cylindrical center section 114A and rounded front and rear cylindrical sections 116A and 118A having generally planar end faces. The front and rear sections 116A and 118A are configured with a diameter greater than the central section 114A, thus forming an area to be grasped by one hand of a field operator. It will be appreciated that the front and rear sections 116A and 118A of the handle 110A are spaced a sufficient distance apart to accommodate a portion of or approximately all of a hand of a user, as best shown in FIG. 1. The handle 110A further includes a longitudinal bore 124A through which the shaft 36A is routed when assembled.

In operation, the handle 110A travels between and is retained by the stop collar contact surface 68A and the base flange contact surface 88A. The mass of the handle 110A and the length of handle travel is such that the probe 22 may be driven into a tree or other wood product a sufficient distance (e.g., ½" to 1" into the fibrous material or cambium of the tree) by approximately two to five strikes of the handle 110A against the base flange contact surface 88A. Of course, it will be appreciated that the force applied by the handle 110A on the base flange contact surface 88A is a function of the acceleration at which the handle 110A is traveling, and may fluctuate from user to user. Thus, two to five strikes is preferably the average number of strikes needed to drive the probe 22 into the wood product a sufficient distance, and thus, the handle 110A may be designed accordingly.

To increase the life of the start measuring probe 22 and to reduce wear on the handle 110A, the stop collar 60A and the base flange 76A, disk-like spacers 130, such as plastic or metallic washers, may be placed in-between the front end of the handle 110A and the base flange contact surface 88A, and the rear end of the handle 110A and the stop collar contact surface 68A. The spacers 130 may be free to slide along the shaft 36A, or may be fixedly connected to the base flange 76A and/or the stop collar 60A, or alternatively, to the retaining flange 40A if the stop collar 60A is omitted. The spacers 130 define planar contact surfaces for engagement against the end faces of the handle 110A.

Figure 3:
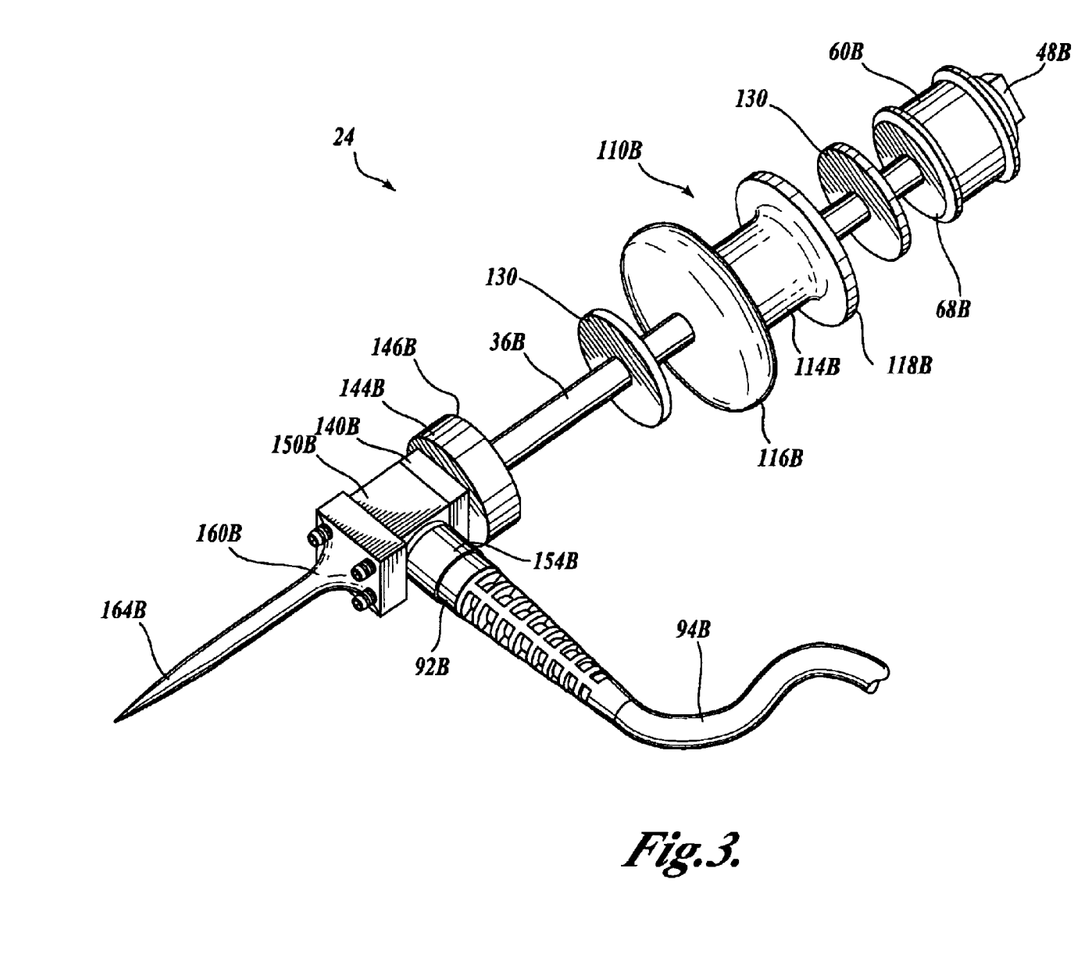
FIG. 3 is a perspective view of an integral measuring probe of the system shown in FIG. 1.
Figure 4:
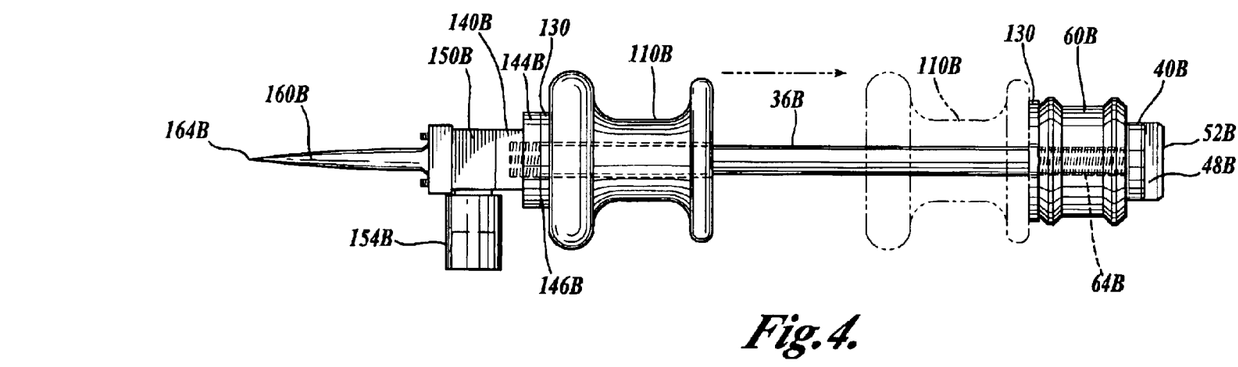
FIG. 4 is a side elevational view of the integral measuring probe of FIG. 3.

Referring now to FIGS. 3 and 4, the system 20 also includes a stop measuring probe 24. The stop measuring probe 24 is constructed substantially identical as the start measuring probe 22 of FIGS. 2, 5, and 6, except for the differences that will now be described in detail. For clarity in the FIGURES and the following description, similar elements of the stop probe 24 will be identified with like numbers having a suffix "B". For example, the shaft of the stop measuring probe will be referenced as "36B."

As best shown in FIGS. 3 and 4, the measuring probe 24 includes a shaft 36B forming a retaining flange 40B at one end. At the other end of the shaft 36B, there is connected a boss 140B having a circumferencially extending flange 144B. The flange 144B defines a contact surface 146B, preferably orthogonal to the longitudinal axis of the shaft 36B. Connected to the boss 140B on the side opposite the shaft 36B is a transducer 150B. The transducer 150B is shock resistant, is designed to detect a stress wave imparted on a wood product such as tree T, and is capable of outputting a signal (e.g., a voltage) indicating the presence of such a stress wave. The transducer 150B further includes a connector fitting 154B for connection to a cooperating connector 92B attached to the end of a flexible sleeve 94B that extends from the measuring probe 24 to the electronic unit. The flexible sleeve 94B surrounds and protects wires or other signal transmitting devices that electrically connect the transducer 150B to the electronic unit. One type of transducer 150B that may be practiced with the present invention is model number SD-02, from Fakopp Enterprises, Agfalva, Hungary. A spike 160B having a penetrating end 164B is secured to the end of the transducer 150B so that the measuring probe 24 may be inserted into the fibrous material of wood products.

Returning to FIG. 1, the system 20 further includes an electrical unit 28 in electrical communication with the transducer of the start measuring probe 22 and the transducer of stop measuring probe 24. The electronic unit 28 determines the time required for the stress wave induced by the impact tool to travel from the start transducer to the stop transducer. The electrical unit 28 includes a timing device and associated circuitry that is configured for receiving a signal from the start transducer and for outputting a signal to the to the timing device for triggering the timing device to start (or obtain a start time) once the signal (e.g. a voltage) received from of the start transducer reaches a threshold value. The circuitry of the electrical unit 28 is further configured for receiving a signal from the stop transducer and for outputting a signal to the timing device for triggering the timing device to stop (or obtain a stop time) once the signal (e.g. voltage) of the stop transducer reaches a threshold value. The elapsed time (or time delta) for the stress wave to travel from the start transducer to the stop transducer as determined by the timing device may be saved in memory and/or displayed on a display device. One electronic unit 28 that may be practiced with the present invention is the Fakopp Microsecond Timer, from Fakopp Enterprises, Agfalva, Hungary.

It will be appreciated that the circuitry of the electronic unit 28 may include a signal amplifier to amplify the voltage of the stop transducer due to attenuation in the induced stress wave. It will be further appreciated by one skilled in the art that the electronic unit 28 may be implemented in a variety of configurations, including but not limited to, analog circuitry using a fixed frequency and a counter, digital circuitry, microprocessors, processing units, combinations thereof, and the like. The memory may included random access memory (RAM), read only memory (ROM), or any other type of digital data storage means.

The electronic unit 28 may further be modified by one skilled in the art for performing other functions for the user. For example, the electronic unit 28 may optionally include a microprocessor or processing unit that calculates the velocity of the stress wave from the elapsed time determined by the timing device. This calculated result or the original elapsed time may then be compared to historical values of similar tree species via look up tables stored in memory for determine an absolute or relative quality rating for the particular tested tree. The results of the comparison may be displayed on the display as a numerical value or percentage. Alternatively, a predetermined threshold value could be programmed in the processor that would simply accept or reject the tree depending on the results of the test. The display for this type of test could be in the form of colored lights. The processor may also have programmable threshold levels for providing a read out of low quality, average quality, high quality, and so forth. Once the quality of the tree is determined, the tree may be marked by paint, indicating the quality of the tree for future identification or use.

A method of using the system 20 will now be described with reference to FIGS. 1–6. As was briefly described above, the system 20 is constructed in accordance with the present invention to be portable, lightweight, and repeatedly used in the field, such as testing a plantation of standing trees. It will be appreciated that testing standing trees has its advantages over testing felled trees, such as less safety concerns, and the ability of thinning the lesser quality trees to the benefit of the higher quality trees, as described above.

To begin, the field operator removably secures the electronic unit 28 to the belt or it may be worn via a strap (not shown) around the neck. Next, the field operator grasps one measuring probe 22 or 24 with a single hand and contemporaneously or subsequently grasps the other measuring probe 22 or 24 with the other hand. When grasping the measuring probes 22 or 24, the field operators hands are wrapped around the respective handles 110A and 110B, with a portion of the hand, such as the pinky and/or ring finger of the hand grasping the base flange 76A and the flange 144B, respectively. Once the system 20 is portably retained by the field operator, the field operator approaches a tree or other wood product to be tested and inserts the first or start measuring probe 22 into the wood product with a stabbing motion to pierce the wood product with the penetrating end 84A of the spike 72A. In one embodiment, the start probe 22 is inserted at an angle between 30–45 degrees to the longitudinal axis of the wood grain of the wood product. To ensure that the penetrating end 84A of the spike 72A is inserted into the fibrous material or cambium of the wood product a sufficient distance (i.e., approximately one-half inch to one inch, depending on the species) the field operator removes their grasp of the flange 76A and slides the handle 110A along the shaft 36A towards the stop collar 60A while the measuring probe 22 remains affixed to the wood product.

The field operator then reverses the direction of the handle 110 prior to impacting the stop collar contact surface 68A (or the spacer 130 if used), thereby striking the end of the handle 110 against the base flange contact surface 88A. The striking force imparted to the base flange contact surface 88 by the handle 110A causes the measuring probe 22 to further penetrate the wood product. This striking motion by the handle 110A may be repeated, if necessary, to reach an appropriate depth within the wood product.

Once the start measuring probe 22 has been inserted into the wood product, the stop measuring probe 24 may be inserted into the wood product a select longitudinal distance from the start measuring probe 22 in a substantially identical manner. The stop measuring probe 24 is preferably inserted with the spike end pointing toward the start measuring probe at an angle of approximately 30–45 degrees to the longitudinal axis of the wood grain of the wood product. Due to the orientation of the inserted probe 24, the field operator may use their index and middle fingers to slide the handle 110B and strike the contact surface 146B. It will be appreciated that the flexible sleeve connecting the start measuring probe 22 to the electronic unit 28 may include a visual gauge or like indicator 180 that represents a known distance from the start measuring probe 22 so that the field operator may insert the stop measuring probe 24 at a pre-selected distance from the start measuring probe 22. This will provide repeatable results and will allow the test results to be directly compared to historical data.

Once the start and stop measuring probes 22 and 24 have been inserted into the wood product, a hammer, mallet or other impact tool I, preferably having a striking surface twice the width or greater than the impact surface 52A of the start measuring probe, is obtained, for example, from a utility belt of the field operator. The field operator then strikes the contact surface 52A of the start measuring probe 22 with the impact tool, which in turn, generates a stress wave through the shaft 36A and the spike 72 and into the fibrous material of the tree. As the stress wave generated by the impact tool travels through the measuring probe 22, the transducer 100A detects the stress wave and transmits a signal to the electronic unit 28. Subsequently, the stress wave travels through the wood product in a longitudinal direction, and is detected by the transducer 150B of the stop measuring probe 24. Once the transducer 150B of the stop measuring probe 24 detects the stress wave, the transducer 150B outputs a signal to the electronic unit 28. The electronic unit 28 receives the signals from the start transducer 100 and stop transducer 150B and determines the travel time of the stress wave if the signals received from the transducers are greater than a pre-selected value. The total elapsed time for the stress wave to travel from the start measuring probe 22 to the stop measuring probe 24 as measured by the timing device of the electronic unit 28 may then be displayed and/or saved in memory. The field operator may then repeat the above striking step with the impact tool I two or three more times to establish an average total elapsed time, if desired.

Once the non-destructive testing of the wood product is complete, and the time of the stress wave is recorded and/or saved in memory, the start and stop probes 22 and 24 are extracted from the wood product. To extract the start and stop measuring probes 22 and 24, the field operator grasps the handles 110A and 110B of each probe with a single hand and moves the handles 110A and 110B rapidly along the shafts 36A and 36B in the direction of the stop collars 60A and 60B to impact the stop collar contact surfaces 68A and 68B in a striking manner, repeatedly if necessary. The striking force of the handles 110A and 110B against the stop collar contact surfaces 68A and 68B dislodges the spikes 72A and 160B from the wood product. Once the start and stop measuring probes 22 and 24 have been extracted from the wood product, the field operator may continue the testing of another wood product.

While the preferred embodiments of the invention have been illustrated and described, it will be appreciated that various changes can be made therein without departing from the spirit and scope of the invention. For example, instead of using a manually driven impact tool, the present invention may be practiced with a separate or integrated impact tool that utilizes a mechanically driven, e.g., spring loaded, or electrically driven, e.g., solenoid, plunger or impact member. Additionally, the measuring probe 22 was described herein as the "start probe" and the measuring probe 24 was described herein as the "stop probe." However, it will be appreciated that the system 20 may interchangeably utilize the measuring probe 22 and the measuring probe 24. For example, the system 20 may comprise two measuring probes 22 (or, alternatively, two measuring probes 24). In this embodiment, one measuring probe 22 (or, alternatively, probe 24) is utilized as the "start" and the other measuring probe 22 (or, alternatively, probe 24) is utilized as the "stop" probe. In another embodiment of the system 20, the measuring probe 22 may be utilized as the "stop" measuring probe, and the measuring probe 24 may be utilized as the "start" measuring probe. Accordingly, it will be appreciated that the electronic unit 28 may be configured by one skilled in the art to allow for the interchangeability of the probes. Further, it will be appreciated that either probe 22 or 24 may be used with other testing systems, or that system 20 may be adapted for testing other wood properties, including the use of more than two measuring probes. In this particular embodiment, the electronic unit 28 may be configured to receive signals from more than two probes and generating a 2-D image for determining such properties as decay, presence of knots, and the like. Thus, the scope of the invention should be determined from the following claims and equivalents thereto.

The embodiments of the invention in which an exclusive property or privilege is claimed are defined as follows:

1. A non-destructive evaluation system for testing wood products, comprising:
   a first integrally formed handheld measuring probe having a body that includes a shaft defining a first impact surface, a spike fixedly coupled to one end of the shaft, a transducer in contact with the spike for detecting a stress wave imparted thereto and outputting a signal indicating the presence of a stress wave, and a handle slideably coupled to the shaft;
   a second integrally formed handheld measuring probe having a body that includes a shaft, a spike fixedly coupled to the shaft, a transducer in contact with the spike for detecting a stress wave and outputting a signal indicating the presence of a stress wave, and a handle slideably coupled to the shaft; and
   an electronic unit including a timing device, the electronic unit coupled in electrical communication with the transducer of the first measuring probe and the transducer of the second measuring probe for receiving the outputted signals therefrom;
   wherein the electronic unit determines the travel time of the stress wave from the transducer of the first probe to the transducer of the second probe.

2. The system of claim 1, wherein the impact surface of the first probe is formed at the end of the first probe shaft.

3. The system of claim 2, wherein the first probe shaft includes a retaining flange disposed at the end of the shaft, the retaining flange having a projection extending in a direction opposite the shaft, the projection forming the impact surface.

4. The system of claim 1, wherein the projection is rounded.

5. The system of claim 2, wherein the first probe impact surface is substantially orthogonal to the longitudinal axis of the shaft.

6. The system of claim 5, wherein the first measuring probe further includes a first contact surface disposed adjacent the impact surface and facing the spike end of the first measuring probe and a second contact surface located at the interface between the shaft and the spike, the first and second contact surfaces slideably retaining the first probe handle therebetween.

7. The system of claim 6, wherein the first or second contact surface is substantially orthogonal to the longitudinal axis of the shaft.

8. The system of claim 6, further including spacers disposed on the opposite sides of the first probe handle, the contact surfaces formed by the spacers.

9. A portable measuring probe comprising:
   a body including a shaft, a spike fixedly coupled to one end of the shaft, a transducer in contact with the spike for detecting a stress wave imparted thereto and outputting a signal indicating the presence of a stress wave, and a handle slideably coupled to the shaft.

10. The probe of claim 9, wherein the shaft defines a first impact surface, the impact surface of the probe being formed at the end of the shaft.

11. The probe of claim 10, wherein the shaft includes a retaining flange disposed at the end of the shaft, the staining flange having a projection extending in a direction opposite the shaft, the projection forming the impact surface.

12. The probe of claim 10, wherein the projection is rounded.

13. A method of testing the stiffness in wood products using a system having a first measuring probe, a second measuring probe, and an electronic unit, each probe having a spike, a shaft rigidly coupled to the spike, first and second contact surfaces at the proximal and distal ends of the shaft, a handle slideably coupled to the shaft between the first and second contact surfaces, and a transducer connected in electrical communication with the electronic unit, the method comprising:
   inserting the spike of the first measuring probe into the wood product;
   driving the spike further into the wood product by sliding the handle in the direction of the spike and impacting the first contact surface;
   inserting the spike of the second probe into the wood product a spaced distance from the first probe;
   driving the spike of the second probe further into the wood product by sliding the second probe handle in the direction of the second probe spike and impacting the first contact surface of the second probe;
   generating a stress wave at the first probe; and
   determining the time taken by the stress wave to travel from the first probe to the second probe.

14. The method of claim 13, wherein the second probe is inserted a known distance from the first probe.

15. The method of claim 13, further including
   measuring a known distance from the first probe prior to inserting the second probe.

16. The method of claim 13, further including
   removing the first probe by sliding the first probe handle in the direction opposite the first probe spike and impacting the second contact surface of the first probe.

17. The method of claim 13, further including removing the second probe by sliding the second probe handle in the direction opposite the second probe spike and impacting the second contact surface of the second probe.

18. The method of claim 13, further including inserting the first and second probes at an angle of approximately 30–45 degrees from the longitudinal axis of the wood grain of the wood product.

19. The method of claim 13, wherein generating a stress wave includes impacting an impact surface formed by the shaft of the first probe.

20. The method of claim 19, wherein impacting the impact surface of the first probe includes impacting the impact surface of the first probe with an impact tool having a striking surface area, wherein the striking surface area is greater than or equal to twice the area of the impact surface.

\* \* \* \* \*